United States Patent [19]

Meyer

[11] 3,936,698

[45] Feb. 3, 1976

[54] ION GENERATING APPARATUS

[76] Inventor: George F. Meyer, 6995 Trolley Way, Playa del Rey, Calif. 90291

[22] Filed: Aug. 27, 1973

[21] Appl. No.: 391,937

Related U.S. Application Data

[63] Continuation of Ser. No. 21,284, March 20, 1970.

[52] U.S. Cl. .............................. 317/4; 317/262 AE
[51] Int. Cl. .............................................. H01j 3/04
[58] Field of Search ........ 317/3, 4, 262 R; 128/190, 128/404; 204/313

[56] References Cited
UNITED STATES PATENTS

| 2,723,349 | 11/1955 | Rylsky | 317/4 |
| 3,624,448 | 11/1971 | Saurenman et al. | 317/4 |

FOREIGN PATENTS OR APPLICATIONS

| 1,319,296 | 1/1963 | France | 317/4 |

*Primary Examiner*—J. D. Miller
*Assistant Examiner*—Harry E. Moose, Jr.
*Attorney, Agent, or Firm*—Ronald W. Reagin

[57] ABSTRACT

An ion generating apparatus and a method of treatment is disclosed which includes means for generating positively charged ions and means for generating negatively charged ions. A timer is provided which alternately energizes the negative ion generator and the positive ion generator in a predetermined time sequence so that the apparatus alternately emits negative ions and positive ions. The patent is thus alternately subjected to a flow of negative and positive ions.

8 Claims, 2 Drawing Figures

INVENTOR.
GEORGE F. MEYER
BY
Ronald W Reagin
ATTORNEY

ION GENERATING APPARATUS

BACKGROUND OF THE INVENTION

This application is a continuation of application Ser. No. 21,284, filed Mar. 20, 1970.

This invention relates to ion generating apparatus and more particularly to apparatus for generating ions to be emitted into the atmosphere for therapeutic purposes.

For many years there has been much research and many reports written about atmospheric ions. Basically these ions are positive and negative electrical charges which are associated with molecules of oxygen, nitrogen and carbon dioxide in the air. Such ions may be generated naturally by cosmic rays, radioactive elements in the soil and air, precipitation, thunderstorms, ultra violet radiation and wind In addition, many artificial or manmade mechanisms also generate such ions. Such mechanisms include X-ray apparatus, very hot surfaces, ultra violet lamps and high voltage devices.

There have been many articles written and published about atmospheric ions and their effect on animals, including human beings. Among other specific claims, researchers report a significant effect of such ions on pulse rate, respiration rate, ph factor of blood, oxygen content of blood, red cell count in blood, skin temperature, basal metabolism, blood pressure, virus invasion and burnt tissue. Most of these reports indicate that negative ions promote good health and that positive ions are either so plentiful that there is no need to add any more to the atmosphere, that they produce discomfort or that they are unhealthy. Negative ions are claimed to relieve asthma, bronchitis, hay fever, headaches and pain associated with burns. Positive ions have been claimed to produce respiratory complaints, aching joints, high altitude sickness, dizziness, fatigue and headaches.

Many different forms of ion generating apparatus have been proposed by those who have done investigations and performed experiments in this area. The proposed apparatus has usually consisted of either means for generating only negative ions or means for generating both positive and negative ions in association with an ion trap for removing the positive ions so generated. In at least one instance, in U.S. Pat. No. 2,264,495, an apparatus is proposed which includes both means for generating positive ions and means for generating negative ions. A sensing device is provided in that patent to monitor the ion level in the atmosphere and to actuate one or the other of the ion generating means depending upon whether the ion level in the atmosphere is above or below a predetermined set level. In any event, the prior art does suggest numerous means for generating ions of various charges, at least some of which are efficient and relatively inexpensive.

In view of the above-mentioned known ion effects and of the availability of ion generating apparatus, it seems surprising that such devices and their use in therapeutic applications has not become widespread. However, it is obviously ture that such devices heretofor have not received widesperad application and their benefits have not been readily available to the public. Probably the primary factor which has retarded the development and use of such apparatus has been that although beneficial results have been reported by reputable experimenters using scientifically accepted standards and techniques, such results have not been obtainable on a repeatable basis. Thus, the same results are not always obtainable by other experimenters following the same techniques and methods and indeed frequently the same experimenters cannot obtain the same results on a repeatable basis even when using the same subjects as patients.

One reason that experiments and techniques which have been reported in the past have not proven to be repeatable is that the atmosphere ions are, of course, electrically charged particles and as such follow all of the basic physical laws of nature which control the behavior of charged particles will neither leave nor enter a metallically shielded space such as is approximated by modern buildings. Further, the behavior of such ions is affected by any electrostatic fields which might be present in the area and they are affected by the humidity of the atmosphere. Further, the attraction of such ions to the body of a patient is a function of the electrostatic voltage of the body of the patient, which is known to vary from time to time even in the same patient. In any event, even when the above conditions are of such a nature to allow negatively charged ions to be attracted to the body of a patient, the body or the clothing of the patient soon takes on a negative electrostatic charge from the very ions with which the patient is being treated and thereafter repels additional negatively charged ions which may be directed at the patient since such repulsion of like electrical charged particles is a basic physical principal.

OBJECTS OF THE INVENTION

It is accordingly an object of the present invention to provide an improved ion generating apparatus.

It is another object of the present invention to provide an improved ion generating apparatus with which more repeatable results can be obtained.

It is still another object of the present invention to provide an improved ion generating apparatus for therapeutic use which overcomes many of the above-discussed defects in the prior art.

It is still another object of the present invention to provide an improved method for treating patients with ions which provides improved therapeutic results for the patient.

BRIEF DESCRIPTION OF THE PRESENT INVENTION

In the present invention it has been discovered that many of the above-discussed defects in the prior art, especially in the area of repeatability, can be overcome by providing an apparatus that is capable of generating both positive and negative ions. This is contrary to the teachings of the prior art which has suggested that only negative ions are beneficial and that positive ions are either unneeded or are harmful. In the presently preferred embodiment of the invention, a timer is provided to alternately energize the positive and negative ion generating apparatus over a predetermined time cycle so that the patient is alternately subjected to positive and negative ion treatment. During the negative portion of the cycle the patient receives all the beneficial results of negative ions which are reported in the prior art. During the positive ion portion of the cycle any negative electrostatic charge on the patient or his immediate environment which resulted from the negative ion portion of the cycle is neutralized and, if desired, the cycle can be extended to actually cause the patient to receive a positive electrostatic charge. Thereafter, in the ensuing negative ion portion of the following cycle the positively charged patient attracts even more negative ions and thus continuously receives the therapeutic benefits of the negative ions as long as the cycle is repeated. The patient thus does not saturate in a condition of repelling the beneficial negative charged ion such as occurs with the prior art devices.

Studies have shown that when patients are so treated, improved therapeutic results are obtained. These studies have particularly shown, for example, that such treatment is quite successful for patients suffering from insomnia.

BRIEF DESCRIPTION OF THE DRAWINGS

For a better understanding of the present invention, together with an appreciation of other objects and advantages thereof, references may be had to the accompanying drawings, in which.

DETAILED DESCRIPTION OF THE PREFERRED EMBODIMENT OF THE INVENTION

Figure 1:
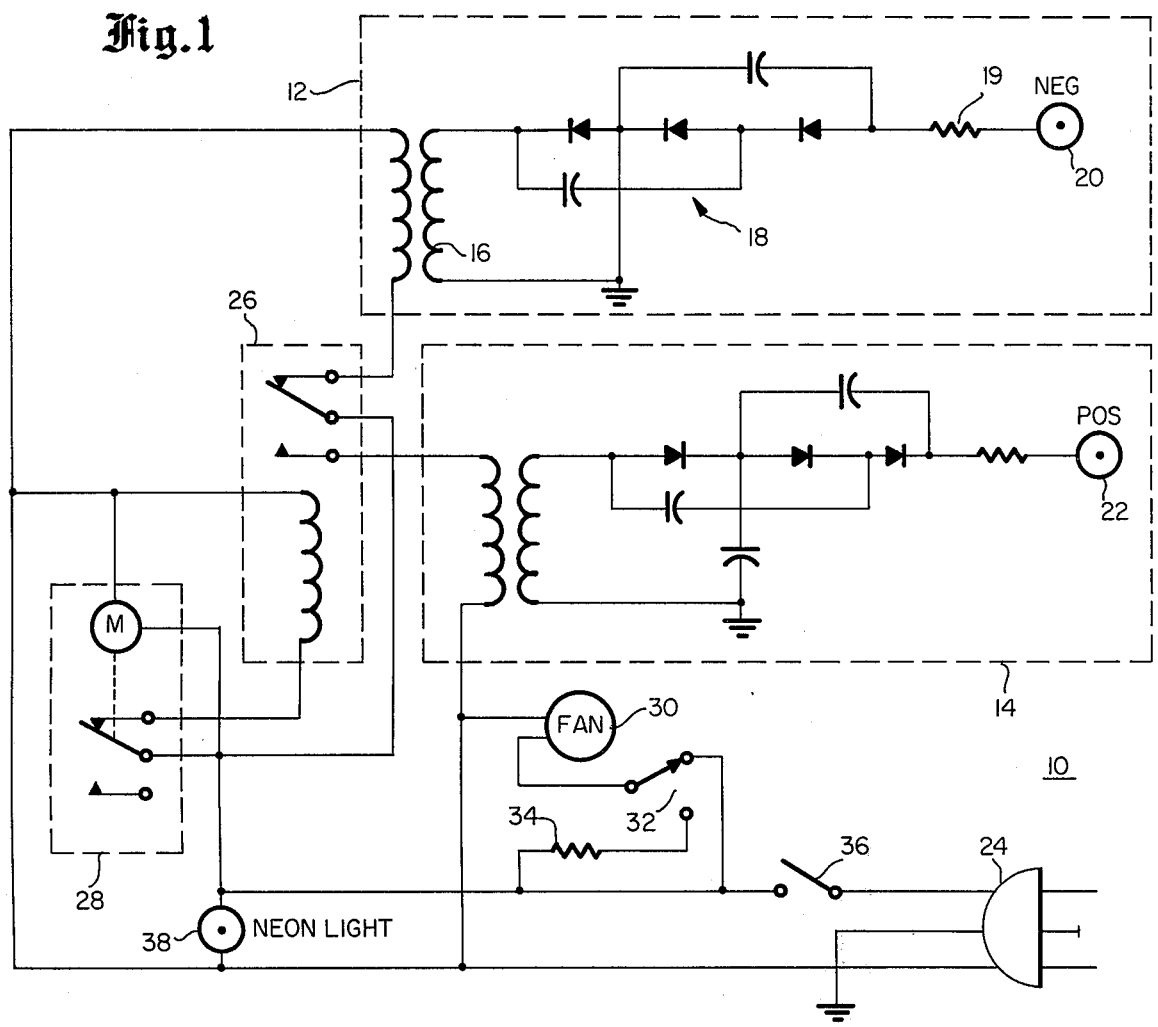
FIG. 1 shows a schematic representation of an ion generating apparatus in accordance with the present invention.

FIG. 1 shows a schematic representation of an ion generating apparatus 10 in accordance with the present invention which includes a negative ion generating section 12 and a positive ion generating section 14. Negative ion generating section 12 includes a power supply consisting of a step-up transformer 16 followed by a capacitor-diode voltage multiplying section 18, the output of which is connected through a resistor 19 to an electrode 20. The operation of the components per se is well known to those skilled in the art and accordingly is not described in detail. Transformer 16 and voltage multiplying section 18 are chosen so that, in the preferred embodiment, a negative voltage of about 4000 volts is applied to electrode 20. Positive ion generating section 14 is similar to negative ion generating section 12 except that the elements of the power supply are oppositely poled to provide a high positive voltage on positive electrode 22.

It is noted at this point that the present invention may use any suitable internal structure of negative ion generating section 12 and positive ion generating section 14. Ion generators of the particular type shown, or any other form of positive and negative ion generators known in the prior art or subsequently developed could be used instead to achieve the desired results in the same manner as does the present invention.

In operation, electrical energy is supplied to the apparatus 10 as through a conventional electrical plug 24. Either the negative generating section 12 or the positive generating section 14 is connected to plug 24 depending upon the state of energization of relay 26. The energization of relay 26 is in turn controlled by timer 28 which is preferably an adjustable timer which can be set to provide any desired time cycle within its limits. Such timers are, of course, well known and readily available. In the shown embodiment timer 28 alternately energizes and deenergizes the coil of relay 26. When relay 26 is energized, as is shown, the primary winding of transformer 16 of negative ion generating section 12 is connected to plug 24 and thus the high negative voltage is impressed upon electrode 20. As timer 28 progresses through its cycle, it subsequently deenergizes relay 26 and at that time positive ion generating section 14, instead of negative ion generating section 12, is connected to plug 24. Then a high positive voltage is impressed upon electrode 22. When timer 28 completes its cycle and begins a subsequent cycle, relay 26 is again energized, thereby disconnecting positive ion generating section 14 from plug 24 and reconnecting negative ion generating section 12 to plug 24.

Apparatus 10 also includes a fan 30, shown schematically, which is always energized with the apparatus regardless of which ion generating section is connected. In the shown embodiment, fan 30 is a two-speed fan capable of either high or low speed operation. Single pole, double throw switch 32 determines the speed of fan 30. Switch 32 is shown in its "fast" position. When switch 32 is in its "slow" position, resistor 34 is connected in series with fan 30, reducing the voltage drop across the fan, thus causing fan 30 to operate at a lower speed.

The purpose of fan 30 is to blow air across electrodes 20 and 22. In the preferred embodiment, as is shown in more detail in FIG. 2 below, electrodes 20 and 22 are located sufficiently close together that a single fan 30 can blow air through or across both of them at the same time. Thus only a single fan need be used. However, it is obvious that if it is so desired, a separate fan could be provided with each of the electrodes 20 and 22.

In the shown embodiment, ion generating apparatus 10 also includes a single pole, single throw switch 36 which serves as an off-on switch for the apparatus and a neon indicator light 38 which indicates whether the apparatus is off or on.

Figure 2:
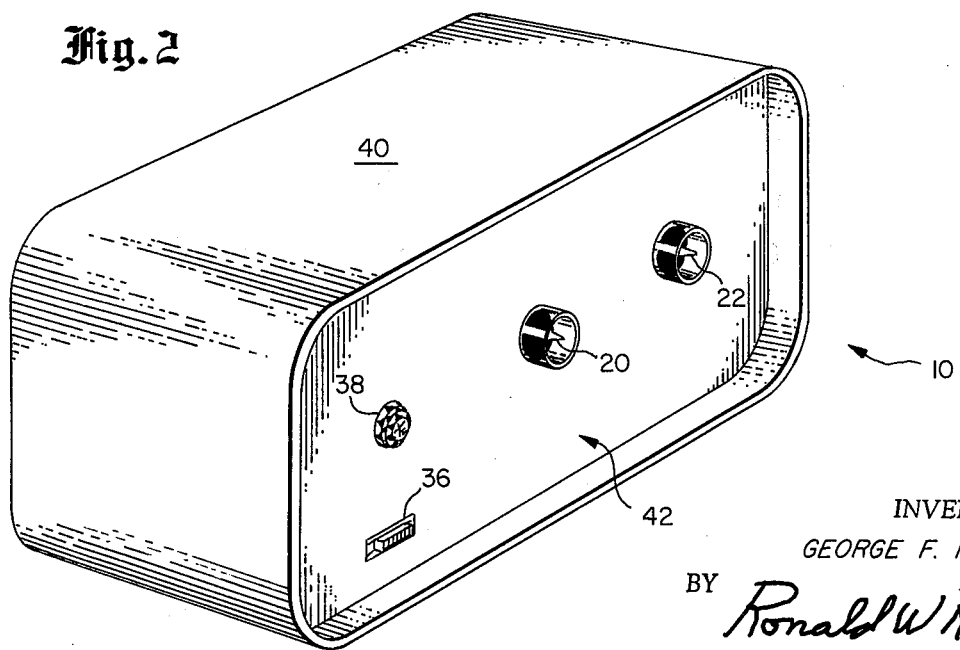
FIG. 2 shows a perspective view of an ion generator in accordance with the present invention and such as is schematically represented in FIG. 1.

FIG. 2 shows a perspective view of an ion generating apparatus 10 in accordance with the present invention and such as is shown schematically in FIG. 1. FIG. 2 shows the housing 40 having a front panel 42 in which is positioned electrodes 20 and 22, off-on switch 36 and indicator light 38. Electrodes 20 and 22 are positioned beside each other so that a single fan 30 (not shown in FIG. 2) positioned inside of housing 40 can blow air across both electrodes.

Ion generating apparatus 10 operates in the following manner: Timer 28 is set to provide a desired operating time cycle. In the presently preferred embodiment of the invention, it has been found that a suitable operating cycle for an average sized home room is about a five-minute cycle. Timer 28 divides the cycle into two equal increments so that during one-half the cycle negative ion generating section 12 is energized and during the other half of the cycle positive ion generating section 14 is energized. Obviously, for a larger sized room it would be desirable to increase the length of the cycle and for a smaller sized room the length of the cycle would be reduced. Also, if it is so desired to do so because of particular local electrostatic conditions or the like. the two portions of the cycle could be of unequal length. Regardless of which polarity ion is being generated, fan 30 blows air across both electrode 20 and electrode 22, thereby serving the dual function of bringing air molecules into contact with the high voltage electrodes, thus generating the ions, and blowing the ions so formed out into the room in which apparatus 10 is located so that a patient may receive the therapeutic benefits of the ions.

During the negative ion portion of the cycle, the patient receives all of the beneficial results of negative ions which are reported in the prior art. During the positive ion portion of the cycle, any negative electrostatic charge on the patient or his immediate environment which resulted from the negative ion portion of the cycle is neutralized, and if desired, the cycle can be extended to actually cause the patient to receive a positive electrostatic charge. Thereafter, in the ensuing negative ion portion of the following cycle, the positively charged patient attracts even more negative ions and thus continuously receives the therapeutic benefits of a negative ion as long as the cycle is repeated. The patient thus does not saturate in a condition of repelling the beneficial negative charged ions such as occurs with prior art devices.

While the invention is thus disclosed and the presently preferred embodiment thereof described in detail, it is not intended that the invention be limited only to the described embodiment. Instead, many modifications will occur to those skilled in the art which lie within the spirit and scope of the invention. For example, any suitable means for generating positive and negative ions may be used with the apparatus other than the particularly described means. Also, the timer may be adjusted to provide any desired timing or operating sequence. It is thus intended that the invention be limited in scope only by the appended claims.

What is claimed is:

1. Ion generating apparatus for exposing a subject such as a patient or the like to an ion flow, comprising, in combination:
   first ion generating means for generating negatively charged ions comprising a first electrode and first power supply means for applying a negative voltage to said first electrode;
   second ion generating means for generating positively charged ions comprising a second electrode and second power supply means for applying a positive voltage to said second electrode;
   means for blowing air across said first and second electrodes; and
   timing means for alternately energizing said first and second power supply means in a predetermined time cycle, said time cycle having a first negative ion emitting time portion and a second positive ion emitting time portion in which said second time portion is sufficiently long to at least neutralize any negative charge accumulated by the subject during said first time portion, whereby the subject does not saturate in a condition of repelling negatively charged ions and continues to receive the benefits of negatively charged ions as long as said apparatus remains energized.

2. The ion generating apparatus of claim 1 in which said first and second power supply means each includes a transformer and a capacitor-diode voltage multiplier section.

3. The ion generating apparatus of claim 1 in which said timing means is adjustable.

4. The ion generating apparatus of claim 1 in which said timing means comprises a timer and a relay means controlled by said timer for alternately energizing said first power supply means and said second power supply means.

5. The ion generating apparatus of claim 2 in which said timing means comprises an adjustable timer and a relay means controlled by said timer for alternately energizing said first power supply means and said second power supply means.

6. The ion generating apparatus of claim 1 in which said first ion generating means comprises a first electrode, and first power supply means for applying a negative voltage to said first electrode, and in which said second ion generating means comprises a second electrode and a second power supply means for applying a positive voltage to said second electrode.

7. The ion generating apparatus of claim 6 which further includes means for blowing air across said first and second electrodes.

8. A method for treating a patient with atmospheric ions which comprises the steps of alternately subjecting the patient to a flow of negatively charged ions for a first predetermined time period and to a flow of positively charged ions for a second predetermined time period in which said second time period is sufficiently long to at least neutralize any negative charge accumulated by the patient during said first time period, whereby the patient does not saturate in a condition of repelling negatively charged ions and continues to receive the benefits of negatively charged ions as long as the treatment is continued.

* * * * *